May 11, 1943. S. B. ROBERTS Plant Pat. 583
ROSE PLANT
Filed Oct. 17, 1942
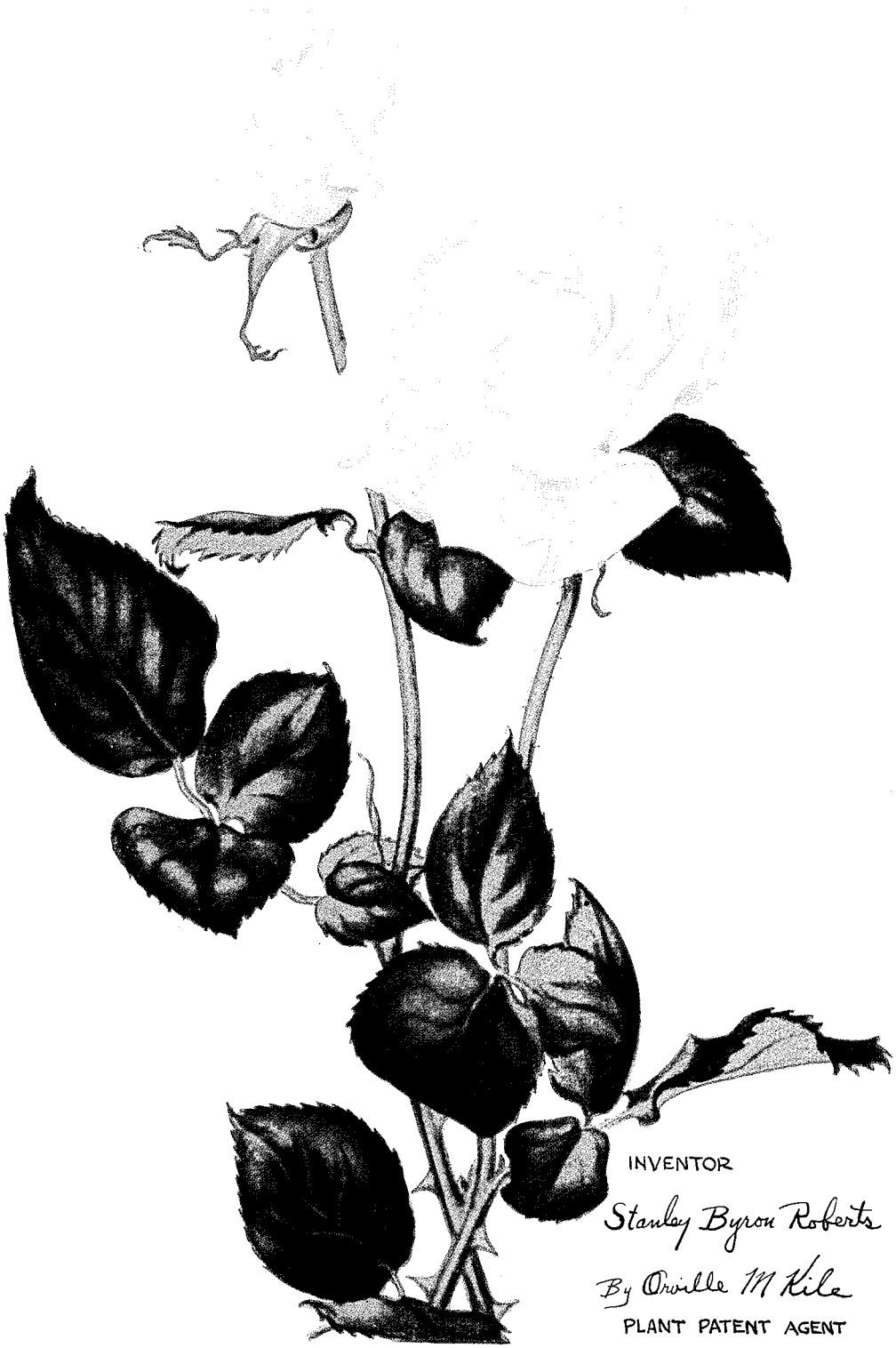
INVENTOR
Stanley Byron Roberts
By Orville M Kile
PLANT PATENT AGENT Patented May 11, 1943

Plant Pat. 583

UNITED STATES PATENT OFFICE

583

ROSE PLANT

Stanley Byron Roberts, Madison, N. J.

Application October 17, 1942, Serial No. 462,384

1 Claim. (Cl. 47—61)

My present invention relates to a new and distinct variety of hybrid tea rose plant, produced by crossing Better Times and Golden Rapture. It is particularly adapted to greenhouse culture and has not been tested for garden use.

The color of the flowers of this variety is outstanding in that it is very bright on the inside of the opening bud and very delicate on the outside of the bud and in its general tone effect after opening.

One of the outstanding features of the blosson is its abundant fragrance. It has the typical rose scent but in much greater abundance than any other indoor rose known to me. The plant is an excellent producer and the blossoms last exceptionally well.

Extensive asexual reproduction of this new variety shows these characteristics to be firmly fixed.

The illustrations making a part of this application show two specimens of the flower with a portion of the stems and foliage—one specimen a bud just beginning to spread and the other a blossom which is almost completely open but with the stamens still covered.

The following detailed description is made from roses grown in my greenhouses at Madison, N. J., cut early in the morning of a hot August day and arriving in Washington, D. C., the same day. Color name and plate references indicate Ridgway's Color Standards and Nomenclature.

*The plant*

Form: Bush. Tall-growing, but not a climber.

Growth: Very vigorous. Easy to grow. Good producer of flowers—as good or better than its parent Better Times. Has not been tested for outside growing.

Foliage: Abundant and disease-resistant. Leaflets 1 to 7.

*Color.*—Deep green, approximately Dark Cress Green (Pl. XXXI) on upper surface, and Bice Green (Pl. XVII) on under surface.

*Appearance.*—Glossy and smooth on upper surface, dull on under surface.

*Size.*—Variable. From 1½ inches long by ¾ inch wide to 2¾ inches long by 1¾ inches wide.

*Shape.*—Oval with acute apex. *Edge.*—sharply and finely serrated.

*Veining.*—Midrib prominent but lateral ribs scarcely noticeable on upper side of leaf.

Rachis: Deeply grooved on upper surface, thorns and spines on under surface.

Stipules: Small, clinging, acute.

Sepals: One or two of the sepals inclined to be foliaceous, others relatively simple. Turn back early and cling to peduncle. Approximately Cress Green (Pl. XXXI) on outer surface and Kildare Green (Pl. XXXI) on inner surface. Outer surface smoth, inner surface pubescent.

Stems: Stiff, strong, heavy, longer than those of its parents and averaging about 18 inches in length.

*Internodes.*—Short, allowing foliage to come close together.

*Thorns.*—Moderate in number; sharp and slender; downward-pointing; light green; irregularly placed.

*Spines.*—Many; covering peduncle, with some also found on under surface of rachis.

*Color.*—Bright, shiny green, approximately Cress Green (Pl. XXXI).

*The flower*

Bud:

*Color.*—Outside is Cameo Pink (Pl. XXVI) in the center of the petal, and approximately Hermosa Pink (Pl. I) on the edges. Inside, clear bright pink. Ridgway's Color Standards has no color approaching this color but the nearest lies between Thulite Pink and Spinel Pink (Pl. XXVI).

*Size.*—Usually 1½ to 2 inches in length.

*Shape.*—Slender; modified urn-shape.

*Peduncle.*—Straight, strong, short, and covered with small spines.

Blossom:

*Color.*—The general color effect of the opened rose is between Cameo Pink and Thulite Pink (Pl. XXVI). Closer examination shows the color to be darker on the edges and lighter toward the center, blending into pale yellow (approximately Straw Yellow, Plate XVI) at the base of the petals. The outside surface of the petals is slightly darker than the inside and does not have such a large yellow base. When the blosson is fully open there is disclosed a large bunch of pistils and anthers, which adds a marked contrast of yellow.

*Discoloration.*—On the second day after opening the colors have softened somewhat and on the third day the blossoms have become an all-over Cameo Pink (Pl. XXVI), with pale yellow at the base of the petals. They hold this delicate pink until the flower dies.

*Form.*—When almost full blown, the form is high centered, but later it opens into cup shape fully revealing the many stamens and pistils.

*Fragrance.*—Very intense and lasting but not heavy. More fragrant than any other indoor rose grown at the present time.

*Longevity.*—Exceedingly good, in fact much better than most of the known roses.

*Size.*—The fully opened flower averages 3½ inches across in August and slightly larger in cooler weather.

*Petalage.*—Although not a thin rose, the petalage is not great. I would call it semi-double. The average number of petals in August is 19.

Petals:

*Texture.*—Substantial but not heavy.

*Shape.*—Slightly cordate. Roll backward slightly when flower is open.

*Size.*—Outer petals approximately 1¾ inches by 1¾ inches.

*Appearance.*—Silky.

*Behavior.*—Cling until flower is very old.

Reproductive organs:

*Pistils.*—Very numerous; tightly bunched. *Styles*—very short and yellowish green. *Stigmas*—red topped with a dot of Mustard Yellow (Pl. XVI).

*Stamens.*—Many; surrounding bunched pistils. *Filaments*—curved inwardly and extending considerably above pistils; Mustard Yellow (Pl. XVI). *Anthers*—large; slightly darker than filaments (approximately Honey Yellow Pl. XXX).

Having thus disclosed my invention, I claim:

The new and useful variety of hybrid tea rose plant as shown and described, characterized particularly by its prolific production of flowers; its very long flower stems; and the splendid lasting qualities, exceptional and abundant fragrance, and delicate but bright pink color of its flowers as indicated.

STANLEY B. ROBERTS.